United States Patent [19]

Manicom

[11] Patent Number: 5,245,996
[45] Date of Patent: Sep. 21, 1993

[54] ANAESTHETIC SYSTEM VALVE FOR CONVERTING BETWEEN MAPLESON 'A', 'D', AND 'E' CONFIGURATIONS

[76] Inventor: Anthony W. Manicom, 173 Blanford Road, Northriding, Randburg, Transvaal, South Africa

[21] Appl. No.: 738,614

[22] Filed: Jul. 31, 1991

Related U.S. Application Data

[63] Continuation-in-part of Ser. No. 458,454, Dec. 28, 1989, Pat. No. 5,070,871.

[30] Foreign Application Priority Data

Dec. 28, 1988 [ZA] South Africa ............... 88/9674
Nov. 22, 1990 [ZA] South Africa ............... 90/9380

[51] Int. Cl.$^5$ ............................................. A62B 9/02
[52] U.S. Cl. ............................ 128/205.24; 128/204.18; 128/205.17
[58] Field of Search ............. 128/204.18, 204.26, 128/205.24, 207.14, 911, 912, 203.12, 205.17

[56] References Cited

U.S. PATENT DOCUMENTS

| | | | |
|---|---|---|---|
| 3,251,359 | 5/1966 | Ismach | 128/205.24 |
| 3,905,362 | 9/1974 | Eyrick et al. | 128/205.19 |
| 3,938,551 | 2/1976 | Henkin | 128/205.24 |
| 4,096,858 | 6/1978 | Eyrick et al. | 128/205.16 |
| 4,180,066 | 12/1979 | Milliken et al. | 128/205.24 |
| 4,245,633 | 1/1981 | Erceg | 128/205.24 |
| 4,249,528 | 2/1981 | Mathes | 128/205.24 |
| 4,281,652 | 8/1981 | Miller | 128/205.17 |
| 4,676,239 | 6/1987 | Humphrey | 128/205.17 |
| 4,694,825 | 9/1987 | Slemmer et al. | 128/205.24 |
| 4,702,240 | 10/1987 | Chaoui | 128/205.24 |
| 4,702,241 | 10/1987 | Gravenstein et al. | 128/205.19 |
| 4,791,922 | 12/1988 | Lindsay-Scott et al. | 128/205.28 |
| 4,846,167 | 7/1989 | Tibbals | 128/202.27 |
| 5,070,871 | 12/1991 | Manicom | 128/204.18 |

FOREIGN PATENT DOCUMENTS

| | | | |
|---|---|---|---|
| 784626 | 8/1979 | South Africa | 128/205.24 |
| 816160 | 8/1981 | South Africa | 128/205.24 |
| 581814 | 10/1946 | United Kingdom | 128/205.24 |
| 602890 | 6/1948 | United Kingdom | 128/205.24 |
| 873006 | 7/1961 | United Kingdom | 128/205.24 |
| 883032 | 11/1961 | United Kingdom | 128/205.24 |
| 1027633 | 4/1966 | United Kingdom | 128/205.24 |
| 1432171 | 4/1976 | United Kingdom | 128/205.26 |
| 1444607 | 8/1976 | United Kingdom | 128/205.26 |
| 1493387 | 11/1977 | United Kingdom | 128/205.26 |
| 2162070 | 1/1986 | United Kingdom | 128/205.26 |

OTHER PUBLICATIONS

*Anaesthesia*, 1983, vol. 38, pp. 361-372, Humphrey, "A New Anaesthetic Breathing System ... ".
"The Johannesburg A-D Circuit Switch", pub. in *The British Journal of Anaesthesia*, (1979), 51, 1185.

Primary Examiner—Edgar S. Burr
Assistant Examiner—Kimberly L. Asher

[57] ABSTRACT

A valve for an anaesthetic rebreathing system includes a valve body, a selector member situated within the valve body and a relief valve which forms an integral part of the valve. The valve can be converted from a Mapleson A to a Mapleson D configuration and from a Mapleson A or D configuration to a Mapleson E configuration. The valve body includes a fresh gas inlet, a fresh gas outlet, a fresh gas conduit in communication with the fresh gas inlet and a fresh gas outlet, an expired gas inlet/outlet port, a waste gas outlet, an expired gas conduit in communication with the expired gas inlet/outlet port and the waste gas outlet, a reservoir bag or ventilator inlet/outlet port and a reservoir bag or ventilator conduit in communication with the reservoir bag or ventilator inlet/outlet port, the conduits converging at a node within which the selector member is movable to isolate the expired gas inlet/outlet port and the waste gas outlet from the reservoir bag or ventilator inlet/outlet port in a first position thereof and to isolate the fresh gas inlet and the fresh gas outlet from the reservoir bag or ventilator inlet/outlet port in a second position thereof, the relief valve, which allows for control of pressure in the expired gas conduit, being adjustable between a first setting in which expired gas may flow freely out of the waste gas outlet and a second setting in which the waste gas outlet is completely occluded, and being adapted, in its second setting, to lock the selector member in the second position.

10 Claims, 3 Drawing Sheets

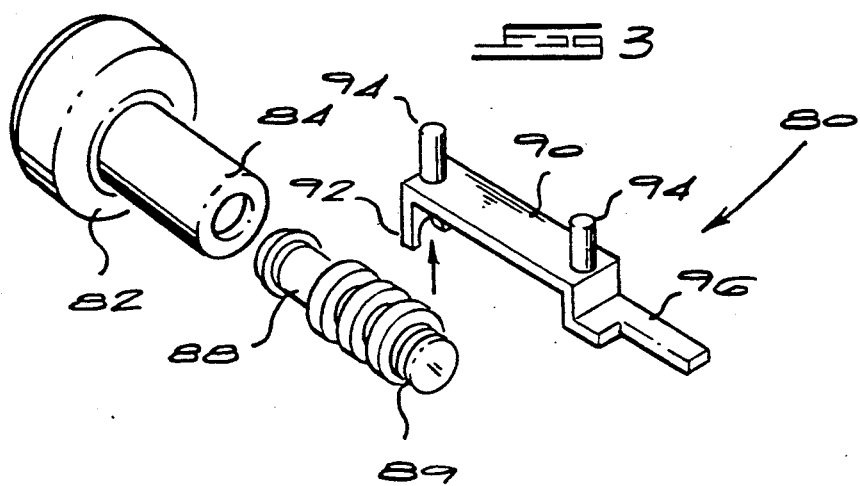
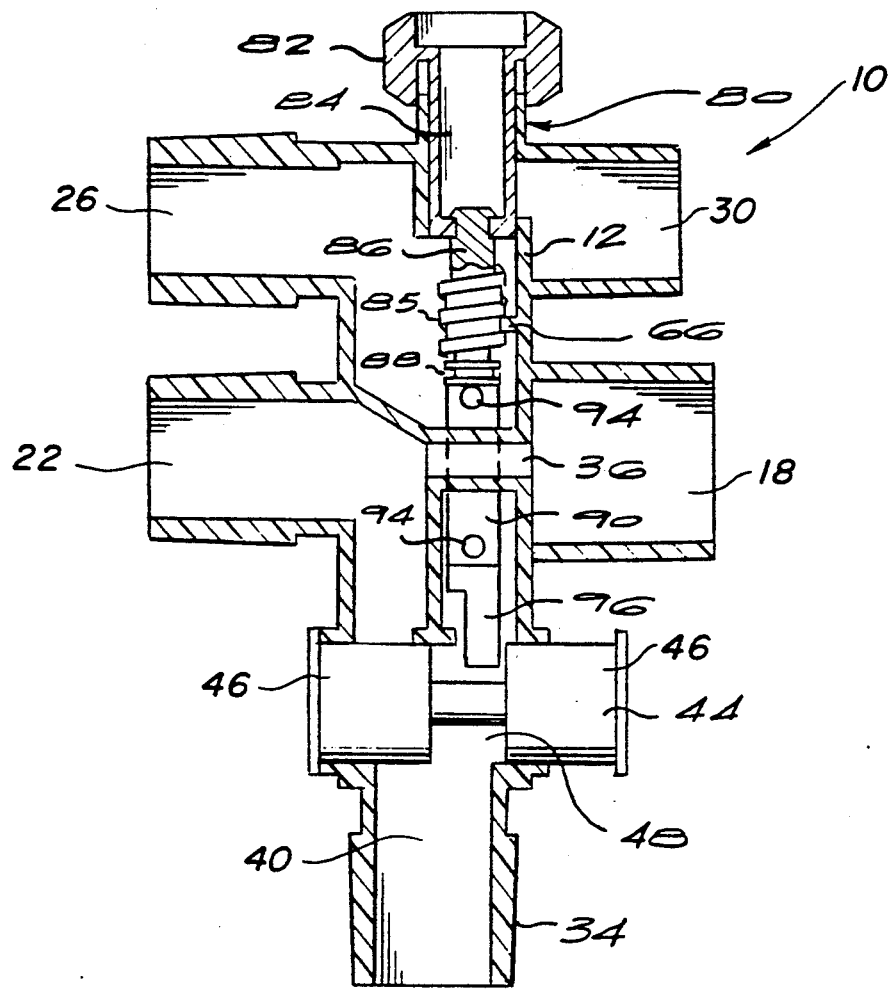

ANAESTHETIC SYSTEM VALVE FOR CONVERTING BETWEEN MAPLESON 'A', 'D', AND 'E' CONFIGURATIONS

CROSS REFERENCE TO RELATED APPLICATIONS

This application is a continuation-in-part of U.S. Ser. No. 07/458,454 filed on Dec. 28, 1989, now U.S. Pat. No. 5,070,871.

BACKGROUND OF THE INVENTION

This invention relates to a valve for an anaesthetic rebreathing system.

The terms "anaesthetic system" and "anaesthetic rebreathing system" are used, in this specification, to denote the connecting apparatus between the anaesthetic machine and the face mask or endotracheal tube which connects to a patient, except where the context indicates otherwise.

A simple anaesthetic breathing system comprises two lengths of flexible tubing of suitable dimensions which connect the patient's airway to an anaesthetic gas supply machine. The two lengths of flexible tubing constitute the inspiratory and the expiratory limbs of a breathing circuit and converge at the patient's airway so that fresh gas flows from the anaesthetic gas supply machine, through the inspiratory limb of the circuit, to the patient's airway. Exhaled gas flows out through the expiratory limb of the circuit and is vented at the end of the expiratory limb. In a simple anaesthetic breathing system therefore, the flow of gas remains unidirectional.

Anaesthetic rebreathing systems have a compliant reservoir bag placed in the circuit for intermittent reversal of gas flow in whichever of the inspiratory or expiratory limbs the reservoir bag is placed. In a Mapleson A, system the inspiratory limb contains the reservoir bag and this configuration is suitable when a patient breathes spontaneously. In a Mapleson D system, the expiratory limb contains the reservoir bag and this configuration is suitable when the breathing of a patient is mechanically or manually controlled, for example by compression of the reservoir bag. Such compression of the reservoir bag results in the rebreathing of exhaled gases which inter alia provides useful humidification in the patient's airway.

A Mapleson E system, like a Mapleson D system, is also suitable when the breathing of a patient is manually or mechanically controlled. However, in a Mapleson E system, the reservoir bag is either open-tailed or is replaced by a mechanical ventilator. In this system the excess gas is vented through a valve or opening external to the breathing circuit itself. A Mapleson D system can easily be converted to a Mapleson E system by closing a relief valve which is in the circuit and by replacing the closed reservoir bag in the expiratory limb with a mechanical ventilator or open-tailed reservoir bag.

It is important that in a particular situation the mode of breathing namely spontaneous breathing or controlled breathing, is appropriate. If the inappropriate mode of breathing is used one or more problems can arise. For example, at least twice the fresh gas flow may be required to prevent retention of carbon dioxide produced by the patient which would be wasteful.

Valve-controlled, switchable rebreathing circuits are known which allow for the selection of a particular mode of breathing. However, an inherent danger of such circuits is that accidental, incorrect use of the valve could have disastrous consequences. For instance, if an open-tailed reservoir bag or a mechanical ventilator was attached to a valve-controlled, switchable circuit in place of the closed reservoir bag, and the selector member was inadvertently moved so that the system was converted to a Mapleson A system, there would be the following undesirable consequences:

a) the patient would be breathing an excessive and dangerous amount of spent gas; and
b) the fresh gas entering the inspiratory limb would simply be vented through the reservoir bag or the mechanical ventilator and would be wasted.

SUMMARY OF THE INVENTION

According to the invention a valve for an anaesthetic rebreathing system includes a valve body, a selector member situated within the valve body and a relief valve which forms an integral part of the valve, the valve body including a fresh gas inlet, a fresh gas outlet, a fresh gas conduit in communication with the fresh gas inlet and a fresh gas outlet, an expired gas inlet/outlet port, a waste gas outlet, an expired gas conduit in communication with the expired gas inlet/outlet port and the waste gas outlet, a reservoir bag or ventilator inlet/outlet port and a reservoir bag or ventilator conduit in communication with the reservoir bag or ventilator inlet/output port, the conduits converging at a node within which the selector member is movable to isolate the expired gas inlet/outlet port and the waste gas outlet from the reservoir bag or ventilator inlet/outlet port in a first position thereof and to isolate the fresh gas inlet and the fresh gas outlet from the reservoir bag or ventilator inlet/outlet port in a second position thereof, the relief valve, which allows for control of pressure in the expired gas conduit, being adjustable between a first setting in which expired gas flows freely out of the waste gas outlet and a second setting in which the waste gas outlet is completely occluded, and being adapted, in its second setting, to lock the selector member in the second position.

The selector member preferably has a reduced central neck region which effectively divides it into two relatively large cylindrical plugs which are adapted to act as two independent closure members, each at its own seat, in the node. This ensures that the reservoir bag or ventilator inlet/outlet port is never completely isolated from the fresh gas inlet, the fresh gas outlet, the expired gas inlet/outlet port and the waste gas outlet simultaneously.

Preferably, the relief valve comprises a valve body and a spindle extending from the valve body, one end of the spindle being receivable within the reduced central region of the selector member when the selector member is in the second position, to lock it into the second position.

The spindle is preferably threaded along at least part of its length, the thread being engageable with a complemental formation defined within the valve body to facilitate controlled movement thereof between the first and second settings, when it is rotated.

The waste gas outlet is adapted for connection to a scavenging system.

The valve is preferably disposable.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DESCRIPTION OF THE DRAWINGS

The present invention will become more fully understood from the detailed description given hereinbelow and the accompanying drawings which are given by way of illustration only, and thus are not limitative of the present invention, and wherein:

FIG. 3 is a pictorial representation of an alternative back pressure control of the invention; and FIG. 4 is a section through a valve of the invention with the selector member positioned to convert the valve to a "Mapleson D" or "Mapleson E" system, and with the back pressure control of FIG. 3 positioned to lock the selector member in this position.

DESCRIPTION OF AN EMBODIMENT OF THE INVENTION

Figure 1:
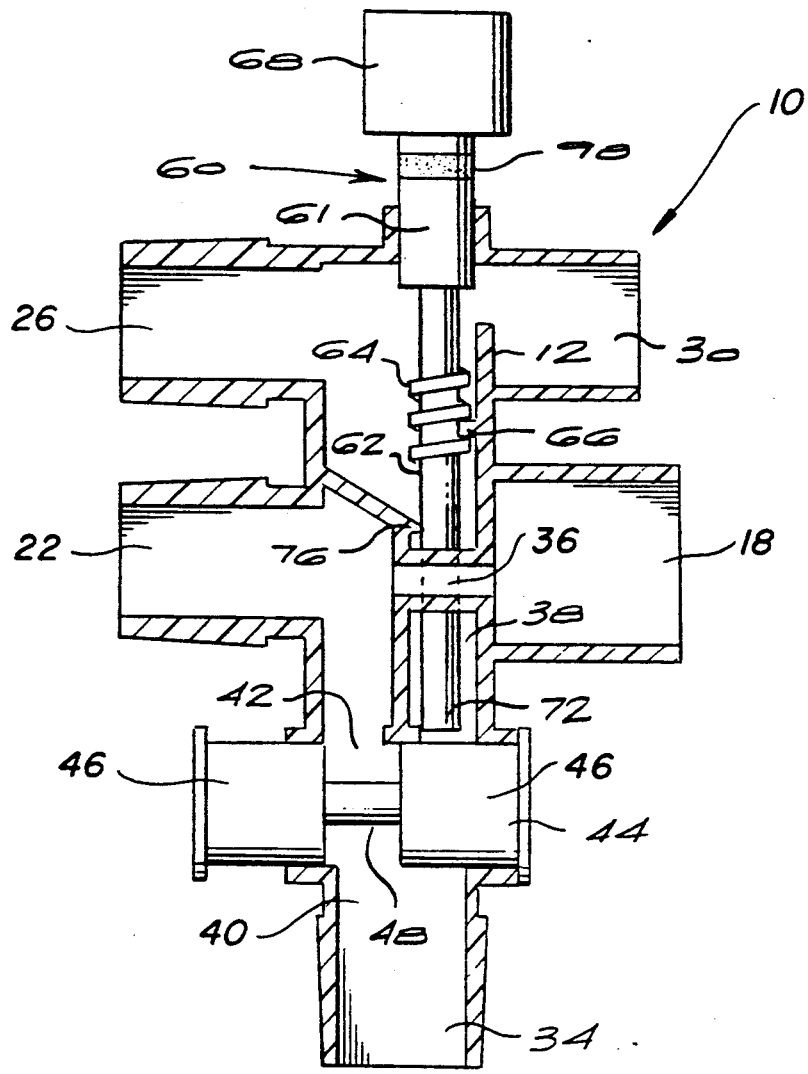
FIG. 1 is a section through a valve of the invention with the selector member positioned to convert the valve to a "Mapleson A" system and with the back pressure control positioned to allow expired gas to flow freely through the waste gas outlet.
Figure 2:
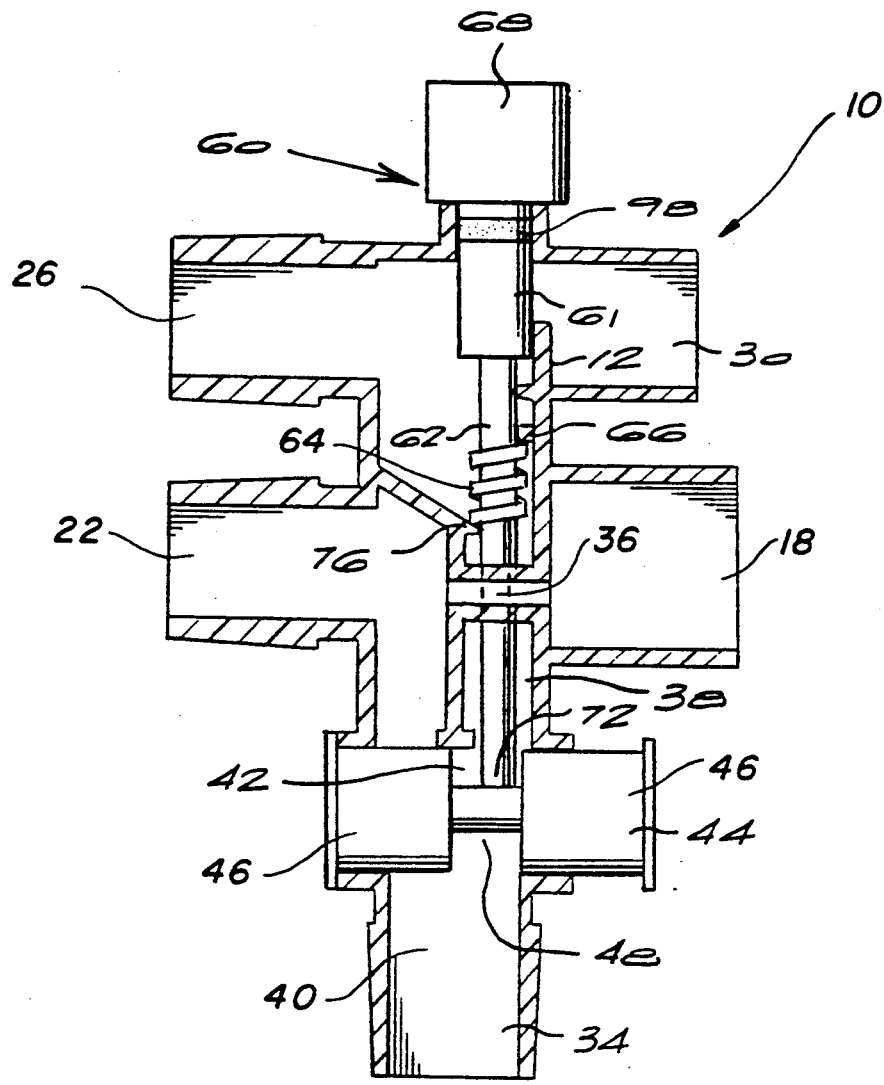
FIG. 2 is a similar section through the valve with the selector member positioned to convert the valve to a "Mapleson D" or "Mapleson E" system and with the relief valve positioned to lock the selector member in this position and simultaneously to occlude the waste gas outlet.

The disposable valve 10 illustrated in FIGS. 1, 2 and 4 is for an anaesthetic rebreathing system and provides for the selection of either a Mapleson A or Mapleson D or a Mapleson E system. It is light, having an injection-moulded plastics body 12, which is formed with:
- a fresh gas inlet 18;
- a fresh gas outlet 22;
- an expired gas inlet/outlet port 26;
- waste gas outlet 30; and
- a reservoir bag inlet/outlet port 34.

The inlet 18, the outlet 22, the port 26, the outlet 30 and the port 34 are all Iso (International Standards Organisation) specification conical fittings. They are also positioned symmetrically about the valve body so as not to produce a twisting force which could loosen the valve from its mounting on the anaesthetic machine gas outlet (not shown).

The valve body 12 has a number of conduits moulded integrally therein. The conduits include:
- a fresh gas conduit 36, which is in communication with the fresh gas inlet 18 and the fresh gas outlet 22;
- an expired gas conduit 38, which is in communication with the expired gas inlet/outlet port 26 and the waste gas outlet 30; and
- a reservoir bag conduit 40, which is in communication with the reservoir bag inlet/outlet port 34.

The conduits all have large cross sectional areas and this allows gas to be conducted with minimal resistance to flow.

All three conduits 36, 38 and 40 converge at a slideway 42 within which a complemental selector member 44 is slidable. The selector member 44 comprises two right circular cylindrical plugs 46 which are joined together by a central neck region 48 of reduced diameter. The right circular cylindrical plugs 46 are hollow-moulded to mitigate jamming, the walls of the plugs being flexible so that the selector member 44 may be easily released by simple manipulation thereof if it becomes jammed in the node 42.

The selector member 44 is slidable between a first and a second position. However, the neck region 48 of the selector member 44 provides a passageway via which all three conduits 36, 38 and 40 are in communication when the selector member 44 is in an intermediate position should an operator not slide the selector member 44 fully either way. This avoids the possibility that the reservoir bag is ever accidently completely isolated from the system and therefore any unexpected increase in the pressure of the gas flow is always partially absorbed by the compliant reservoir bag and never transmitted directly to the patient.

The closure member 44 allows for conversion of the system to one of three breathing systems, a Mapleson A, a Mapleson D or a Mapleson E system, by simply sliding the selector member 44. In existing devices, which employ rotatable stopcocks, a twisting force is applied to the valve which could lead to accidental disconnection from the anaesthetic machine.

The valve 10 also includes a relief valve 60 or 80, as illustrated in FIGS. 1 and 2 and in FIGS. 3 and 4 respectively. The relief valve 60 or 80 forms an integral part of the valve 10 and is not carried on the expiratory limb. Therefore, it does not, due to its weight, produce a turning moment on the valve 10 which may also lead to disconnection should the system be bumped accidentally. The relief valve 60 or 80 is adjustable between a first setting, in which expired gas may flow freely out of the waste gas outlet and a second setting in which the waste gas outlet is completely occluded. It may also be adjusted to one or more other settings in which the waste gas outlet is at least party occluded. In the first setting, the back pressure in the expired gas conduit is maintained at a relatively low level and in the remaining settings the outflow of the expired gas is at least partially restricted to maintain the back pressure in the expiratory limb of the system at a predeterminable, higher level.

The relief valve 60, illustrated in FIGS. 1 and 2, comprises a valve body 61 and spindle 62. The spindle 62 has a screw thread 64 formed along part of its length. The screw thread 64 engages with a complemental formation 66 extending from the anaesthetic valve body 12 into the expired gas conduit 38. Rotation of a knob 68, attached to the valve body 61, causes the spindle 62 either to advance into or to retreat from the expired gas conduit 38, depending on the direction of rotation, in a controlled manner.

FIG. 1 shows the selector member 44 in the first position. This corresponds to a Mapleson A system configuration-spontaneous breathing in the patient-with the fresh gas inlet 18 and the fresh gas outlet 22 in communication with the reservoir bag inlet/outlet port 34. A constant stream of fresh gas enters the valve 10 via the fresh gas inlet 18, flows down the fresh gas conduit 36, through the reservoir bag inlet/outlet port 34 and into the reservoir bag (not shown). From there fresh gas flows back up the fresh gas conduit 36 and out of the fresh gas outlet 22 which leads to the inspiratory limb (not shown) of the anaesthetic system. Expired gas flows from the expiratory limb (not shown) of the anaesthetic system through the expired gas inlet/outlet port 26, into the expired gas conduit 38 and out of the waste gas outlet 30. The relief valve 60 is withdrawn and does not occlude the waste gas outlet 30.

When the selector member 44 is positioned to convert an anaesthetic circuit to a Mapleson A system-spontaneous breathing in the patient, as is the case in FIG. 1, the advancement of the spindle 62, by rotation of the knob 68, into the conduit 38 will be prevented by the selector member 44 itself.

FIG. 2 shows the selector member 44 in the second position. This corresponds to a Mapleson D or E system configuration-controlled breathing in the patient-with the expired gas inlet/outlet port 26 and the waste gas outlet 30 in communication with the reservoir bag inlet/outlet port 34. This allows a constant stream of fresh gas to enter the valve 10 via the fresh gas inlet 18 but prevents it from flowing through the reservoir bag inlet/outlet port 34 into the reservoir bag. The fresh gas flows into the fresh gas conduit 36 and out of the fresh gas outlet 22 which leads to the inspiratory limb of the anaesthetic system. Expired gas flows from the expiratory limb of the anaesthetic system, through the expired gas inlet/outlet port 26 and into the expired gas conduit 38. Some of this gas flows out through the waste gas outlet 30, which may be partly occluded by the relief valve 60. The remainder of the expired gas flows down the expired gas conduit 38 through the reservoir bag inlet/outlet port 34 and into the reservoir bag.

A colored band 98 is painted around the body 62 or 84 of the release valves 60 or 80 of the invention. When the valves 60 or 80 are in-the unlocked position, the colored band 98 is clearly visible and acts as a warning that the anaesthetic valve must be used with a closed reservoir bag attached, namely in a Mapleson A or Mapleson D system. When the valves are in the locked position, the band 98 is not visible and an open-tailed reservoir bag or ventilator can safely be attached to the port 34, namely a Mapleson E system.

When the selector member 44 is positioned to convert an anaesthetic circuit to a Mapleson D or E system, as is the case in FIG. 2, the spindle 62 can be advanced into the conduit 38, by rotation of the knob 68, until its end 72 is received within the reduced central neck region 48 of the selector member 44. In this position therefore, the spindle 62 itself prevents movement of the selector member 44 within the slideway 42 from the Mapleson E to the Mapleson A position. Thus, the only way that anaesthetic valves of the invention can be placed in the Mapleson A configuration is by causing the spindle 62 to retreat from the expired gas conduit 38 by rotating the knob 68 in the reverse direction thereby unlocking the valve control member 44.

This procedure exposes the colored band 98 to warn a user that a closed reservoir bag must be attached. Thus, the anaesthetic valves of the invention have the following safety advantages: The locking mechanism of the relief valve will indicate clearly when the valve has been altered from Mapleson D to E configuration; and The selector member 44 cannot inadvertently be moved from the Mapleson E configuration thereby eliminating the risk of selecting the Mapleson A configuration without a closed reservoir bag being attached. The attendant risks to a patient of such incorrect use of the valve are thus reduced.

Thus, although other mechanisms may be converted from D to E configurations, by closing the relief valve and moving the reservoir bag, it is hazardous to do this if the switching mechanism is still operational. This is because the Mapleson A configuration must never be used without a closed reservoir bag attached. Accidental selection of the A configuration without a reservoir bag being attached, results in dangerous loss of fresh gas (and rebreathing) without any obvious warning that the system is operating incorrectly. The present valve, having a separate E configuration, has a major advantage over other A/D selector mechanisms.

The alternative relief valve 80 shown in FIGS. 3 and 4 comprises a knob 82, a valve body 84 and a spindle 86. The spindle 86 comprises a first segment 88 and a second segment 90. The first segment 88, in the assembled configuration of the valve 80, is held captive within the body 84. The segment 88, like the spindle 62 illustrated in FIGS. 1 and 2, has a screw thread 85 defined thereon which engages with the complemental formation 66 defined in the anaesthetic valve body 12 to allow for advancement or retreat of the spindle 86 within the expired gas conduit 38. The second segment 90 has a yoke 92 formed in one of its ends. The yoke 92 fits over the free end 89 of the first segment 88 and allows the first segment 88 to rotate relative to the second segment 90 when the knob 82 is rotated.

The second segment 90 has two upstanding locating pins 94 extending from it which, when the valve 80 is assembled, locate on either side of the fresh gas conduit 36 and define a distance through which the second segment can be moved. A stepped formation 96 projects from the other end of the second segment 90. The stepped formation 96, like the end 72 of the spindle 62, locates in the reduced central neck region 48 of the selector member 44 when it is in the Mapleson E position and locks it in this position.

The component parts of the valve 10 are arranged so as to facilitate correct attachment of the valve and to provide a symmetrical unit with its center of gravity close to the fresh gas port. The valve 10, after normal attachment to an anaesthetic gas supply machine is oriented in such a way that the inspiratory and expiratory limbs point towards the patient with the reservoir bag dependent.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

I claim:

1. A valve for an anaesthetic rebreathing system including a valve body, a selector member situated within the valve body and a relief valve which forms an integral part of the valve for an anaesthetic rebreathing system, the valve body including a fresh gas inlet, a fresh gas outlet, a fresh gas conduit in communication with the fresh gas inlet and the fresh gas outlet, an expired gas inlet/outlet port, a waste gas outlet, an expired gas conduit in communication with the expired gas inlet/outlet port and the waste gas outlet, one of a reservoir bag and ventilator inlet/outlet port and one of a reservoir bag and ventilator conduit in communication with the one of the reservoir bag and ventilator inlet/outlet port, the conduits converging at a node within which the selector member is movable to isolate the expired gas inlet/outlet port and the waste gas outlet from the one of the reservoir bag and ventilator inlet/outlet port in a first position thereof and to isolate the fresh gas inlet and the fresh gas outlet from the one of the reservoir bag and ventilator inlet/outlet port in a second position thereof, the relief valve controlling pressure in the expired gas conduit and being adjustable between a first setting in which expired gas flows freely out of the waste gas outlet and a second setting in which the waste gas outlet is completely occluded, and the relief valve in the second setting locking the selector member in the second position.

2. The valve according to claim 1, wherein the selector member has a reduced central neck region which divides the selector member into two relatively large cylindrical plugs which act as two independent selector members, each at a seat thereof in the node.

3. The valve according to claim 2, wherein the selector member is movable between a first, an intermediate and a second position, the selector member, when in the intermediate position thereof allowing the fresh gas inlet, the fresh gas outlet, the expired gas inlet/outlet port and the waste gas port all to be in communication with the reservoir bag inlet/outlet port.

4. The valve according to claim 3, wherein the node is a slideway, shaped complementally to the selector member, the selector member being slidable within the slideway between the first, the intermediate and the second positions, the fresh gas conduit, the expired gas conduit and the reservoir bag conduit all open into the slideway so that when the selector member is in the intermediate position all the conduits are interconnected via the reduced central neck region of the selector member.

5. The valve according to claim 3, wherein the relief valve comprises a valve body and a spindle extending from the valve body, one end of the spindle being receivable within the reduced central neck region of the selector member, when the selector member is in the second position, to lock the selector member into the second position.

6. The valve according to claim 5, wherein the spindle is threaded along at least part of the length thereof, the thread being engageable with a complemental formation defined within the valve body for controlled movement of the spindle between the first and second settings of the relief valve, by rotation of the spindle.

7. The valve according to claim 5, further comprising a marking on the relief valve visible when the relief valve is in one of the first and second settings but failing to be visible when the valve is in other settings, visibility of the marking indicating whether the valve is correctly configured for a Mapleson E system.

8. The valve according to claim 2, wherein each plug is deformable so that the selector can be released by deformation of the plugs should the selector become jammed in the node.

9. The valve according to claim 7, wherein each plug is hollow-moulded.

10. The valve according to claim 1, wherein the valve is a plastics material made by injection moulding and wherein the valve is disposable.

* * * * *